(12) United States Patent
Gordon et al.

(10) Patent No.: US 9,697,920 B2
(45) Date of Patent: Jul. 4, 2017

(54) SHIELDING DEVICE AND METHOD

(71) Applicant: Radux Devices LLC, Omaha, NE (US)

(72) Inventors: Gregory Gordon, Omaha, NE (US); Douglas Scott Wahnschaffe, Monticello, MN (US)

(73) Assignee: Radux Devices, LLC, Omaha, NE (US)

( * ) Notice: Subject to any disclaimer, the term of this patent is extended or adjusted under 35 U.S.C. 154(b) by 49 days.

(21) Appl. No.: 14/491,499

(22) Filed: Sep. 19, 2014

(65) Prior Publication Data
US 2016/0027540 A1  Jan. 28, 2016

Related U.S. Application Data

(60) Provisional application No. 62/028,896, filed on Jul. 25, 2014.

(51) Int. Cl.
| | | |
|---|---|---|
| A61B 6/10 | (2006.01) | |
| G21F 1/02 | (2006.01) | |
| G21F 3/00 | (2006.01) | |
| A61B 90/00 | (2016.01) | |

(52) U.S. Cl.
CPC ............... *G21F 3/00* (2013.01); *A61B 6/107* (2013.01); *A61B 90/05* (2016.02); *G21F 1/02* (2013.01); *A61B 2090/0436* (2016.02); *A61B 2090/0481* (2016.02)

(58) Field of Classification Search
CPC .............. A61B 6/107; A61B 6/10; G21F 3/00
See application file for complete search history.

(56) References Cited

U.S. PATENT DOCUMENTS

| | | | |
|---|---|---|---|
| 2,497,749 A | | 2/1950 | Wagner |
| 3,016,255 A | * | 1/1962 | Russell .................. E05B 3/003 |
| | | | 292/352 |
| 3,239,669 A | | 3/1966 | Weinberger |
| 3,303,717 A | * | 2/1967 | Valenti ..................... G05G 1/10 |
| | | | 411/509 |
| 3,883,749 A | | 5/1975 | Whittaker et al. |
| 4,220,867 A | | 9/1980 | Bloch, Jr. |
| 4,751,747 A | | 6/1988 | Banks et al. |

(Continued)

FOREIGN PATENT DOCUMENTS

| | | |
|---|---|---|
| CA | 2091608 | 9/1994 |
| EP | 1526603 | 4/2005 |

(Continued)

OTHER PUBLICATIONS

Health Physics Society, "Lead Garments (Aprons, Gloves, etc.)," hps.org [online], Aug. 13, 2014 [retrieved on Jan. 12, 2015]. Retrieved from the Internet: <URL: http://hps.org/publicinformation/ate/faqs/leadgarmentsfaq.html>, 8 pages.

(Continued)

*Primary Examiner* — Nicole Ippolito
*Assistant Examiner* — Sean Luck
(74) *Attorney, Agent, or Firm* — Fish & Richardson P.C.

(57) ABSTRACT

Some embodiments of a shielding device can include a base and a shield coupled to the base. The shielding device can be used to provide protection for a healthcare worker (e.g., physician, nurse, technician) during a medical procedure.

10 Claims, 17 Drawing Sheets

(56) References Cited

U.S. PATENT DOCUMENTS

| | | | |
|---|---|---|---|
| 4,872,714 A * | 10/1989 | Brusasco | E05B 81/14 292/201 |
| 4,917,413 A * | 4/1990 | Jason | E05C 19/066 292/76 |
| 4,938,233 A | 7/1990 | Orrison, Jr. | |
| 5,125,115 A | 6/1992 | Lincoln | |
| 5,319,349 A * | 6/1994 | Smith, III | A45F 5/02 24/11 M |
| 5,523,581 A | 6/1996 | Cadwalader | |
| 5,569,090 A * | 10/1996 | Hoskins | F16D 3/18 403/311 |
| 5,628,062 A | 5/1997 | Tseng | |
| 5,638,545 A | 6/1997 | Rosner | |
| 5,704,662 A * | 1/1998 | Kwiatkowski | E05B 17/2023 292/194 |
| 5,711,027 A | 1/1998 | Katz et al. | |
| 5,992,823 A * | 11/1999 | Hung-Lin | F16K 5/061 251/315.1 |
| 6,135,032 A * | 10/2000 | Ko | A47B 9/083 108/147.21 |
| 6,217,087 B1 * | 4/2001 | Fuller | E05B 55/00 292/33 |
| 6,394,724 B1 * | 5/2002 | Kelly | F16B 41/002 411/107 |
| 7,226,234 B2 * | 6/2007 | Gordy | F16C 11/04 403/141 |
| 7,521,615 B1 * | 4/2009 | Ho | G10D 3/14 84/304 |
| 8,015,714 B2 | 9/2011 | Dekort et al. | |
| 8,032,994 B2 * | 10/2011 | Waddell | B63B 17/02 24/103 |
| 8,334,524 B2 | 12/2012 | DeMeo et al. | |
| 8,445,093 B2 | 5/2013 | Lemer | |
| 2003/0132639 A1 * | 7/2003 | Franklin | E05B 17/005 292/288 |
| 2003/0209387 A1 * | 11/2003 | Burr | E06C 7/14 182/129 |
| 2004/0169114 A1 * | 9/2004 | Dierkes | F16M 13/02 248/165 |
| 2004/0183316 A1 * | 9/2004 | Walls | E05B 63/04 292/336.3 |
| 2005/0023842 A1 * | 2/2005 | Johnson | E05C 19/18 292/294 |
| 2005/0104435 A1 * | 5/2005 | Bain | A47C 1/03 297/411.36 |
| 2008/0056813 A1 * | 3/2008 | Viernekes | F16D 1/027 403/311 |
| 2008/0128297 A1 | 6/2008 | Rose | |
| 2008/0182093 A1 | 7/2008 | Sonntag et al. | |
| 2010/0289718 A1 * | 11/2010 | Kang | H01Q 1/1207 343/882 |
| 2011/0288489 A1 | 11/2011 | Bierman et al. | |
| 2012/0132217 A1 | 5/2012 | Rees | |
| 2012/0246790 A1 | 10/2012 | Salcedo | |
| 2012/0324614 A1 | 12/2012 | Steinberg et al. | |

FOREIGN PATENT DOCUMENTS

| | | |
|---|---|---|
| FR | 2439460 | 5/1980 |
| JP | 2010-525910 | 7/2010 |
| JP | 2013-015369 | 1/2013 |
| KR | 2009030459 A | 3/2009 |
| WO | WO 2005/094272 | 10/2005 |
| WO | WO 2012/049469 | 4/2012 |
| WO | WO 2015/042419 | 3/2015 |

OTHER PUBLICATIONS

Naidu et al., "Radiation exposure to personnel performing endoscopic retrograde cholangiopancreatography," *Postgrad Med J.*, 81(960):660-662, Oct. 2005.

Whitby and Martin, "Investigation using an advanced extremity gamma instrumentation system of options for shielding the hand during the preparation and injection of radiopharmaceuticals," *J Radiol Prot.*, 23(1):79-96, Mar. 2003.

International Search Report for PCT/US2014/056565 mailed Aug. 23, 2015, 13 pages.

Mettler et al., "Radiologic and Nuclear Medicine Studies in the United States and Worldwide: Frequency, Radiation Dose, and Comparison with Other Radiation Sources-1950-2007," Radiology, Nov. 2009, 253(2): 520-531.

International Preliminary Report on Patentability for International Application No. PCT/US2014/056565, mailed Feb. 9, 2017, 10 pages.

* cited by examiner

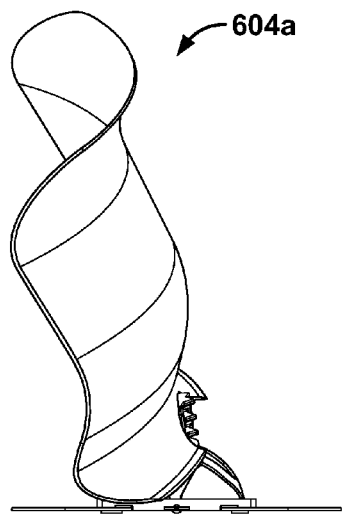
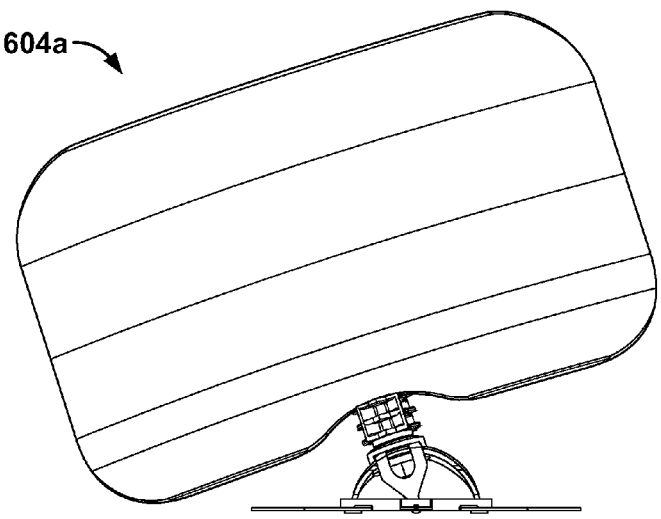
FIG. 6A  　　　　　　　　FIG. 6B
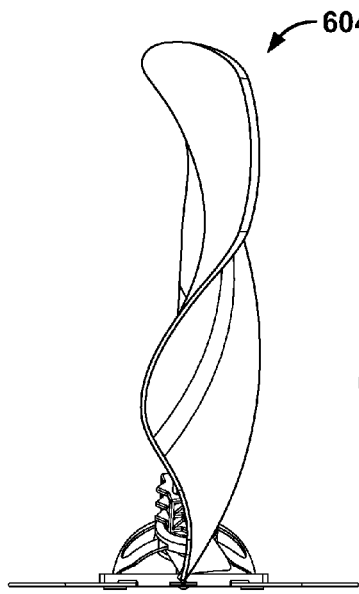
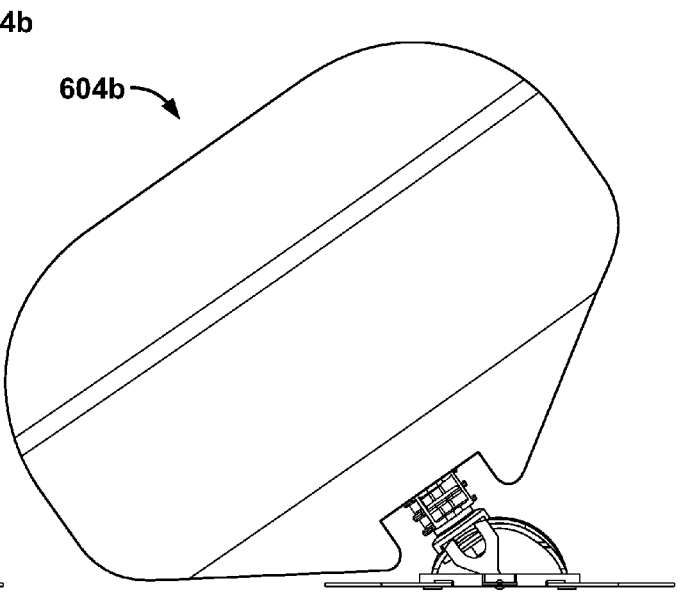
FIG. 6C  　　　　　　　　FIG. 6D

SHIELDING DEVICE AND METHOD

CROSS-REFERENCE TO RELATED APPLICATIONS

This application claims the benefit of U.S. Provisional Application Ser. No. 62/028,896, filed Jul. 25, 2014. The disclosure of the prior application is considered part of (and is incorporated by reference in) the disclosure of this application.

TECHNICAL FIELD

This document relates to shielding devices, such as portable radiation shielding devices for use in a medical environment.

BACKGROUND

In many situations, an interventional radiologist or other healthcare worker (e.g., a physician, nurse, technician) may work under a radiation field (e.g., from a fluoroscope, X-rays, other imaging system, or the like) when treating a patient. Although significant measures are often taken to minimize a patient's exposure to radiation during medical procedures, the healthcare worker implementing the procedure is often left exposed to the radiation—at least to some degree—and such exposure is often repeated for each new patient. For example, a healthcare worker's hands can be exposed to radiation from radiation imaging machines while inserting a central line in a patient (e.g., during a fluoroscopic procedure). Physical barriers can be used to shield the healthcare worker from radiation exposure, but often they are bulky and disruptive to the healthcare worker during the procedure.

SUMMARY

Some embodiments of a shielding device can be used to provide protection for a healthcare worker (e.g., physician, nurse, technician) during a medical procedure. In such circumstances, a shield of the shielding device can be manipulated to a user-selected orientation relative to a base, and optionally, the shield may then locked in the selected position so as to provide a radiation block for the healthcare worker's hands that would otherwise be within the radiation field from the real-time X-Ray imaging apparatus. In addition to the shielding device protecting the healthcare worker's hands from X-Ray radiation, the shield can further provide physical protection for the healthcare worker from spatter of blood or other bodily fluids that may occur during the procedure—all while allowing the healthcare worker to position his or her hands in a non-disruptive and ergonomically effective manner.

In some embodiments, a radiation shielding device may include a radiation shield and a base. The base may include a substructure attachable to an object, and a retainer structure attachable to the radiation shield. Optionally, the base can include a lock device that is actuatable to lock the shield in a selected angular position after adjusting the shield device relative to the base.

Particular embodiments described herein include a method of shielding radiation during a medical procedure. The method may include coupling a base of a radiation shielding device to an object proximate a radiation source. The method may also include coupling a shield of the radiation shielding device to the base. Optionally, the angle of the shield relative to the base of the shielding device and the object can be adjusted to a user-selected orientation and then the shield can be locked in place at the selected angular position. The method may further include shielding radiation from the radiation source as the medical procedure is conducted.

In some embodiments, a radiation shielding device includes a radiation shield and a base, and the base may include a substructure attachable to an object, and a retainer structure attachable to the radiation shield. Optionally, the retainer structure may include an adjustable coupling comprising first and second semi-spherical yokes oriented perpendicular to one another in an overlapping manner. Additionally or alternatively, the retainer structure may optionally include an adjustable coupling operable between an unlocked condition in which an angular position of the shield is adjustable to a user-selected position, and a locked condition in which the angular position of the shield is substantially fixed. Additionally or alternatively, the radiation shield may optionally have a contoured shape providing a skewed reverse curve profile along its height. Additionally or alternatively, the radiation shield may optionally comprise a material having radiation shielding properties (such as barium sulfate), and the radiation shield may have a density of about 1.5 $g/cm^3$ to about 2.5 $g/cm^3$.

In some embodiments, a radiation shielding device may include a radiation shield having a height of about 5 cm to about 25 cm and a maximum thickness of about 1 mm to about 5 mm. Also, the radiation shield can comprise a material having radiation shielding properties. The device may also include a base that includes a substructure attachable to an object, and a retainer structure attachable to the radiation shield.

The details of several embodiments are set forth in the accompanying drawings and the description below. Other features, objects, and advantages of the invention will be apparent from the description and drawings, and from the claims.

BRIEF DESCRIPTION OF THE DRAWINGS

FIGS. 6A-B are side and perspective views of a shield device in accordance with additional embodiments.

FIGS. 6C-D are side and perspective views of a shield device in accordance with further embodiments.

DETAILED DESCRIPTION OF ILLUSTRATIVE EMBODIMENTS

Figure 1A:
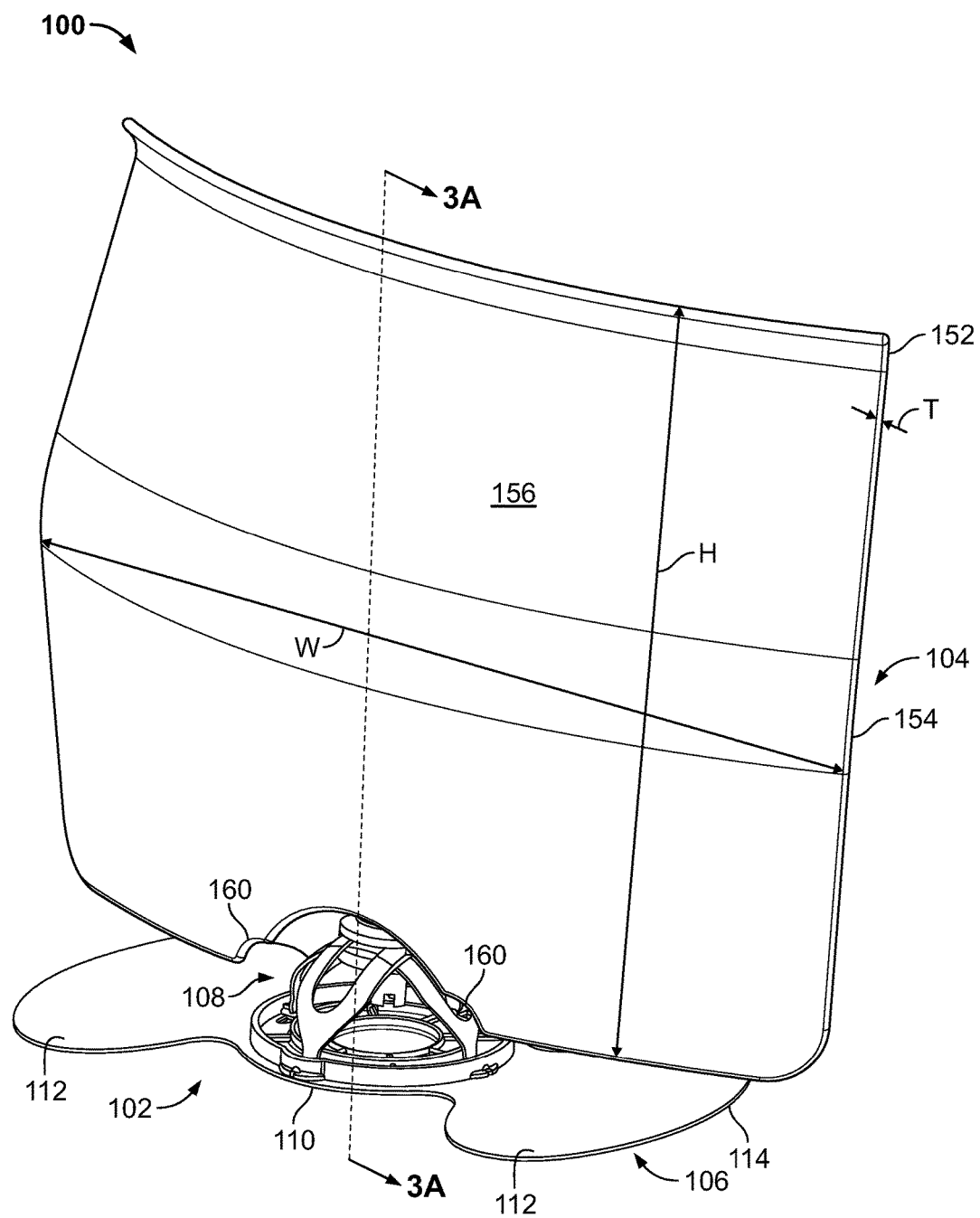
FIGS. 1A-C are perspective front, perspective rear, and top views of a shielding device in accordance with some embodiments.
Figure 1B:
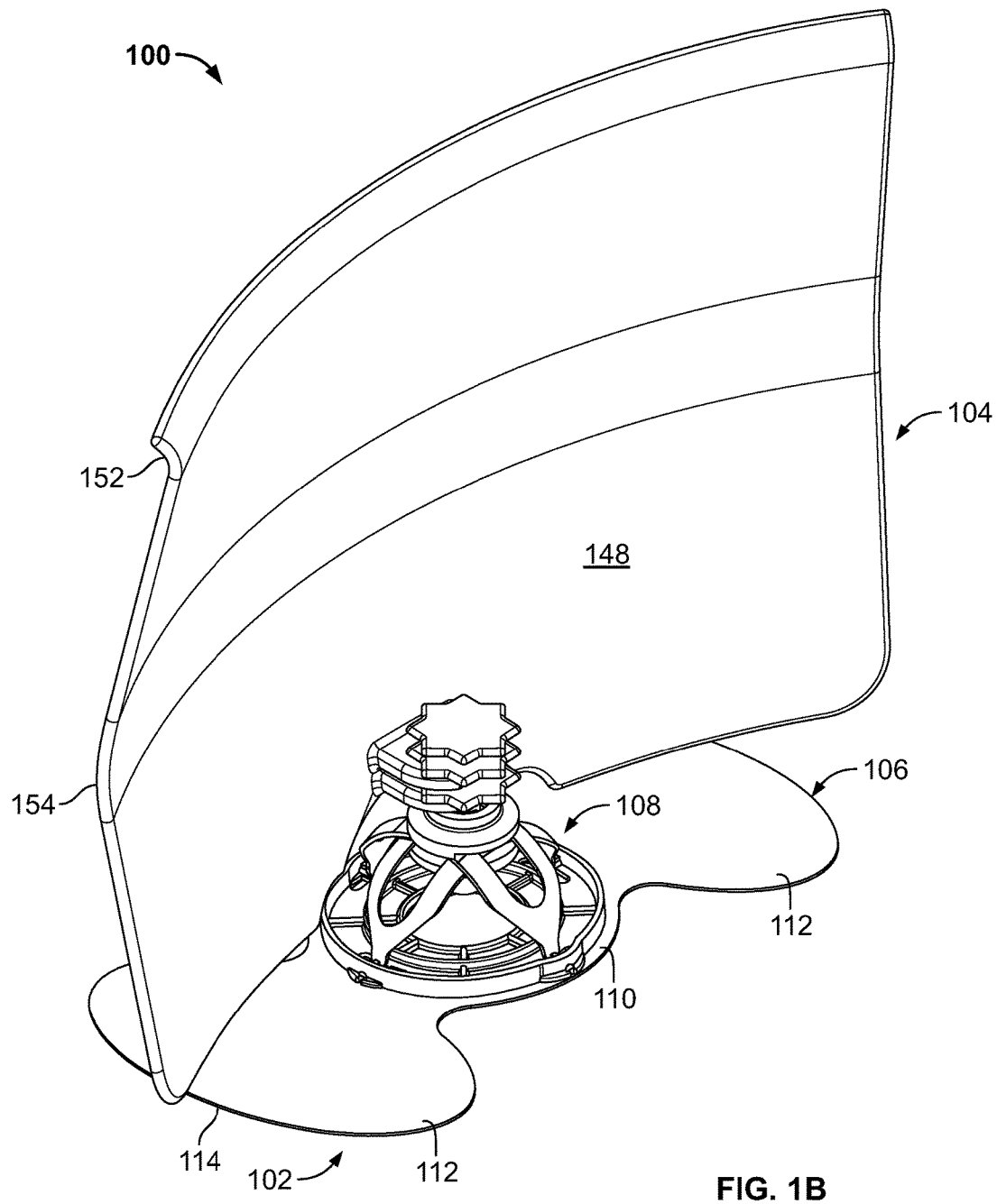
Figure 1C:
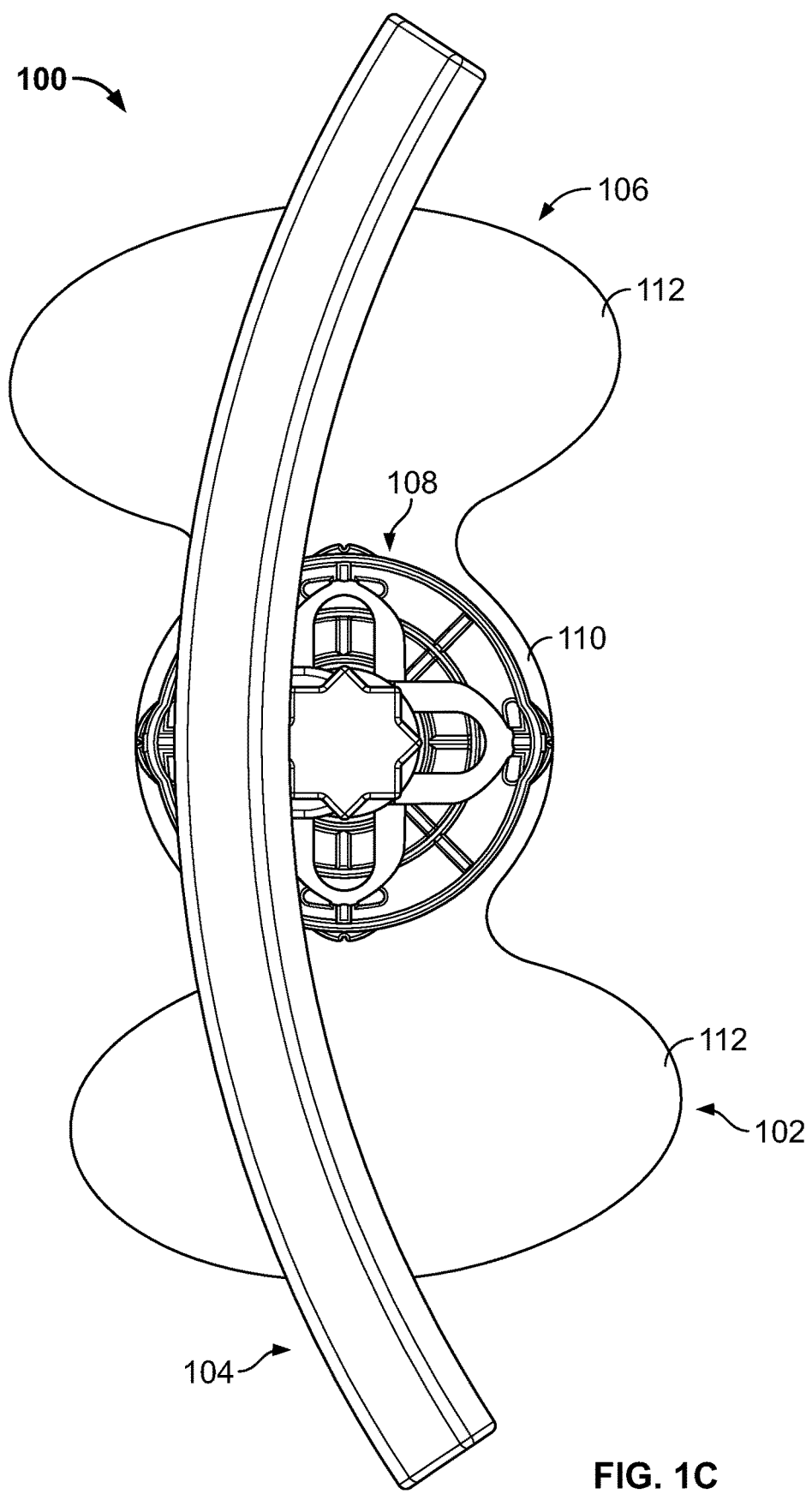

Referring to FIGS. 1A-C, some embodiments of a shielding device 100 can include a base 102 and a shield 104 coupled to the base 102. The shielding device 100 can be used to provide protection for a healthcare worker (e.g., physician, nurse, technician) during a medical procedure. As one example, the base 102 of the shielding device 100 can be adhered to a patient's skin positioned near the patient's liver when inserting a bile drain using real-time X-Ray imaging. In such circumstances, the shield 104 can be manipulated to a user-selected orientation relative to the base 102 and then locked in the selected position so as to provide a radiation block for the healthcare worker's hands that would otherwise be within the radiation field from the real-time X-Ray imaging apparatus. In addition to the shielding device 100 protecting the healthcare worker's hands from X-Ray radiation, the shield 104 can further provide physical protection for the healthcare worker from spatter of blood or other bodily fluids that may occur during the procedure—all while allowing the healthcare worker to position his or her hands in a non-disruptive and ergonomically effective manner.

In some applications, protecting portions of the healthcare worker's body nearest to the source of radiation, such as the worker hands, can be beneficial because radiation exposure decreases based on the distance from the source. Thus, a healthcare worker's hands, if not protected, may be exposed to nine times the radiation to which his/her torso is exposed during an X-Ray imaging procedure. In some applications, the shielding device 100 is provided as a portable structure that can be transported to the site of a medical procedure (e.g., an exam room or an operating room) by the healthcare worker and disposed of at the conclusion of the procedure to prevent the transmission of pathogens between patients and/or healthcare workers.

As shown, the base 102 of the shielding device 100 includes a substructure 106 and a retainer structure 108. During use of the shielding device 100, the substructure 106 supports the base 102 on the surface of an object (not shown) and the retainer structure 108 couples the base 102 to the shield 104. In various applications of the shielding device 100, the supporting object may include a portion of the patient's skin along an exposed body part of the patient (e.g., a limb or a torso) or any other object that is capable of firmly carrying the base 102 and the attached shield 104 (e.g., a table, a bed rail, or the like). In some applications, the supporting object may include a portion of the healthcare worker's body, e.g., a hand or an arm.

The construction of the substructure 106 provides sufficient mechanical strength and stiffness for supporting the base 102 on the surface of the object in a substantially fixed position during use (e.g., as the shield 104 is being coupled to the base 102 or otherwise manipulated by a healthcare worker). In this embodiment, the substructure 106 includes a butterfly-shaped, generally flat member having a circular central body 110 extended by opposing oval-shaped wings 112. The central body 110 of the substructure 106 is attached to the retainer structure 108 (and, optionally, can be continuous such that it extends under the entirety of the retainer structure 108 (refer to FIG. 2)). The wings 112 provide additional surface area for contacting the supporting object (e.g., so as to more firmly adhere or otherwise attached with the patient's skin or other supporting object). In some embodiments, the substructure 106 can include a compliant member capable of conforming to various contours and corners of the supporting object. For example, in this embodiment, the wings 112 can be bent out of plane to follow the shape of the object. In some embodiments, the substructure 106 can include a malleable wire frame to reinforce the compliant member.

In some embodiments, the substructure 106 is fabricated from one or more plastic materials capable of accepting an infusion of radiation shielding material (e.g., material including barium, lead, tungsten, tin, aluminum and/or any attenuating metal). In some embodiments, the substructure 106 can include a laminated multi-layer construction. For example, the substructure 106 can include a skin-friendly underlayer (e.g., a foam layer) bonded to a reinforcing overlayer (e.g., a flexible metal or plastic layer). In some embodiments, the substructure 106 is fabricated from one or more materials that are suitable for medical applications (e.g., biocompatible metallic and/or polymeric materials). For example, the substructure 106 can be fabricated from a medical grade dense foam sheet material having a thickness of about 1 millimeter to 2.5 centimeters. In some embodiments, a bottom surface 114 of the substructure 106 can include an adhesive material suitable for temporarily adhering the base 102 to the supporting object. The adhesive can be a medical grade adhesive that is resistant to water, blood, and other bodily fluids, and that is suitable for adhering to the exterior of a targeted skin surface. In some embodiments, the adhesive on the bottom surface 114 may initially be covered by a removable sheet to expose the adhesive for use. Various types of suitable attachment mechanisms can be used to couple the substructure 106 to the supporting object. For example, in some embodiments, the substructure can include a suction device or an adjustable strap system to attach the substructure to the object. In some embodiments, the substructure can be provided in the form of a glove or a strap system wearable by the healthcare worker while performing a medical procedure (e.g., a fluoroscopic diagnostic procedure to evaluate for aspiration).

As noted above, the retainer structure 108 couples the base 102 to the shield 104 during use. In some embodiments, the retainer structure 108 provides an adjustable coupling that permits movement of the shield 104 with at least two degrees of freedom (and, in some embodiments, three degrees of freedom). As such, the shield can be positioned at numerous angles relative to the substructure 106 of the base 102 (and therefore the supporting object). In some embodiments, the coupling of the retainer structure 108 can be operated between an unlocked condition, where the angular position of the shield 104 is adjustable to a user-selected position, and a locked condition, where the angular position of the shield 104 is fixed.

Figure 2:
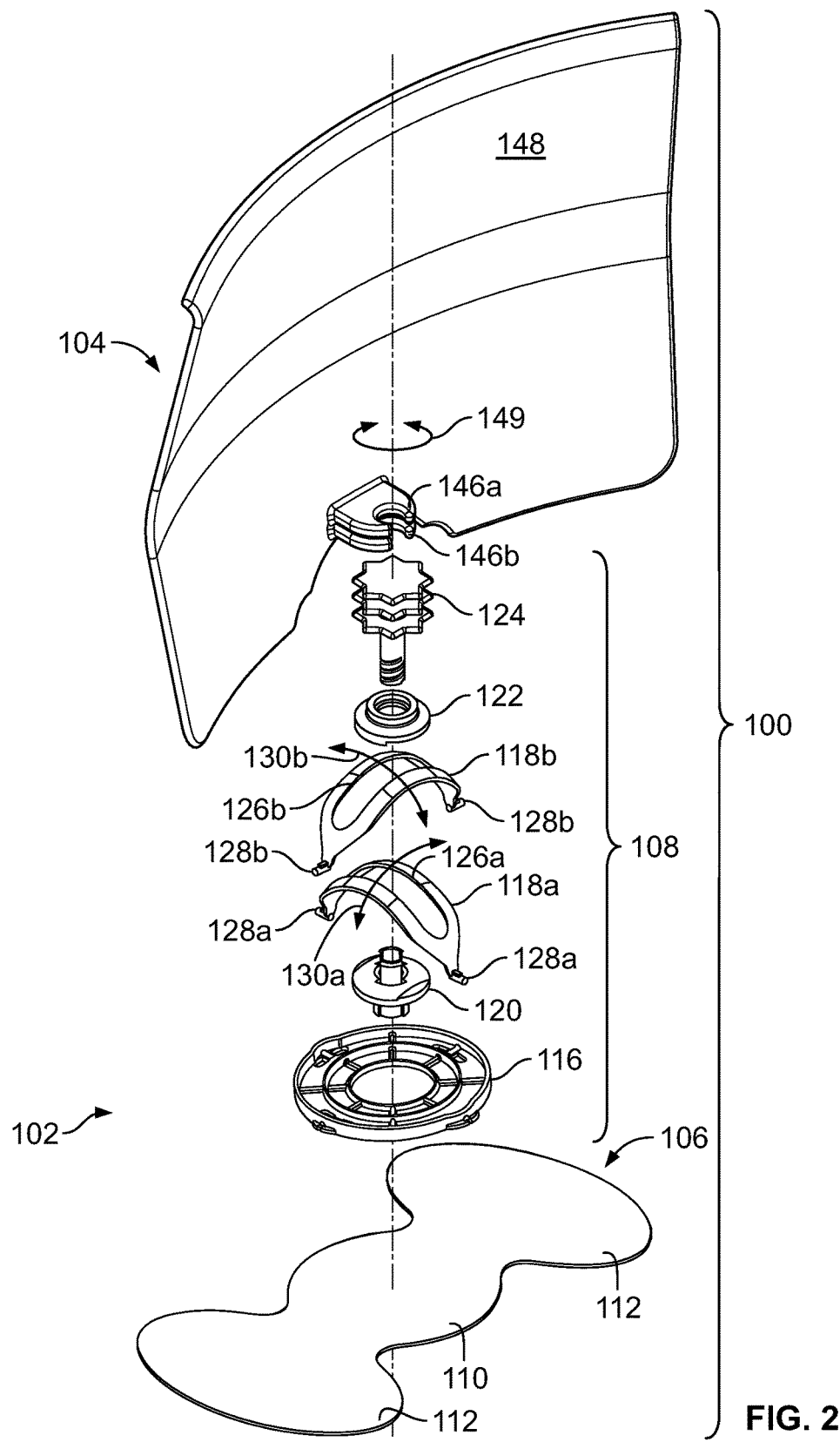
FIG. 2 is an exploded perspective view of the shielding device of FIGS. 1A-C.
Figure 3A:
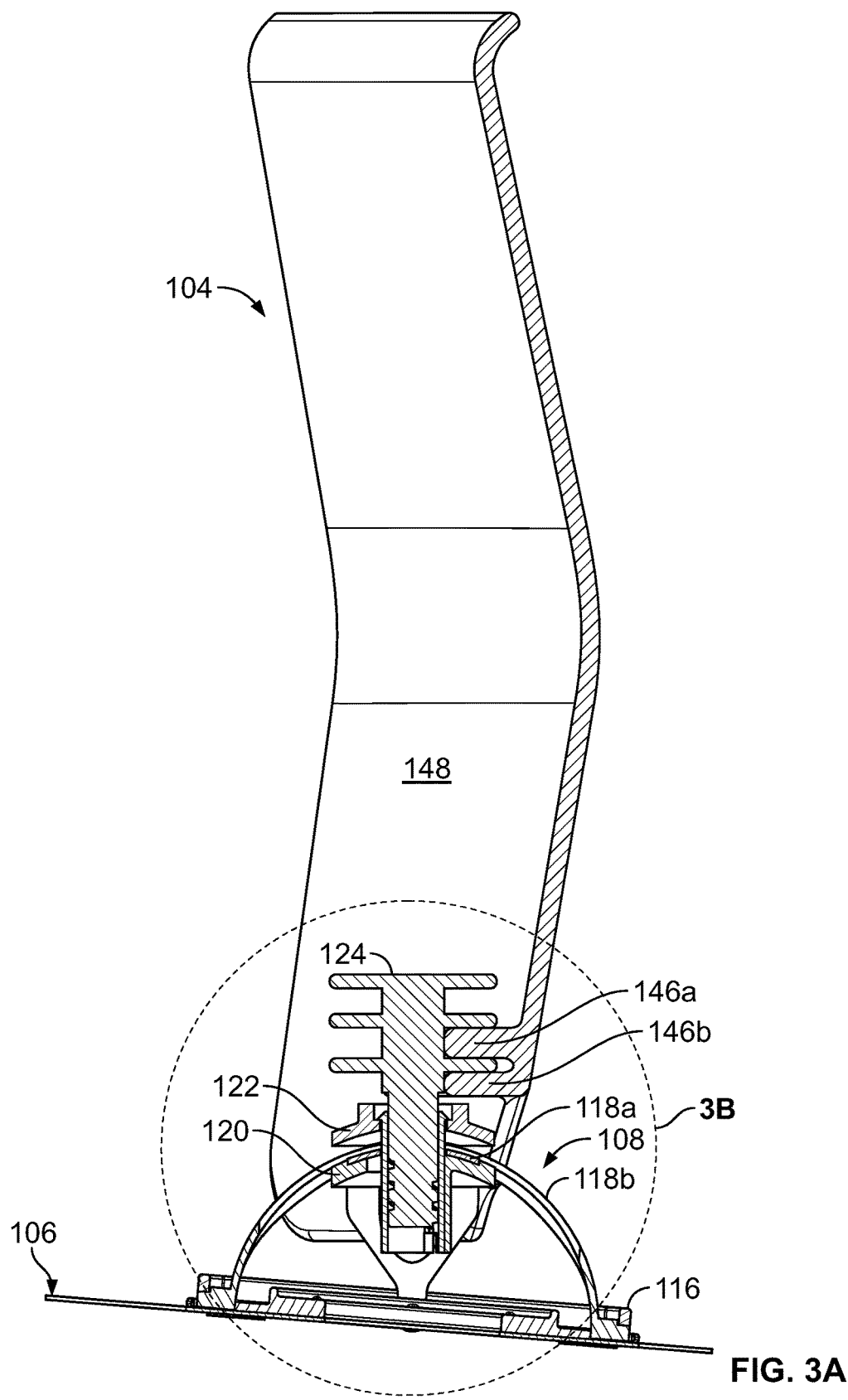
FIG. 3A is a cross-sectional view of the shielding device of FIGS. 1A-C.
Figure 3B:
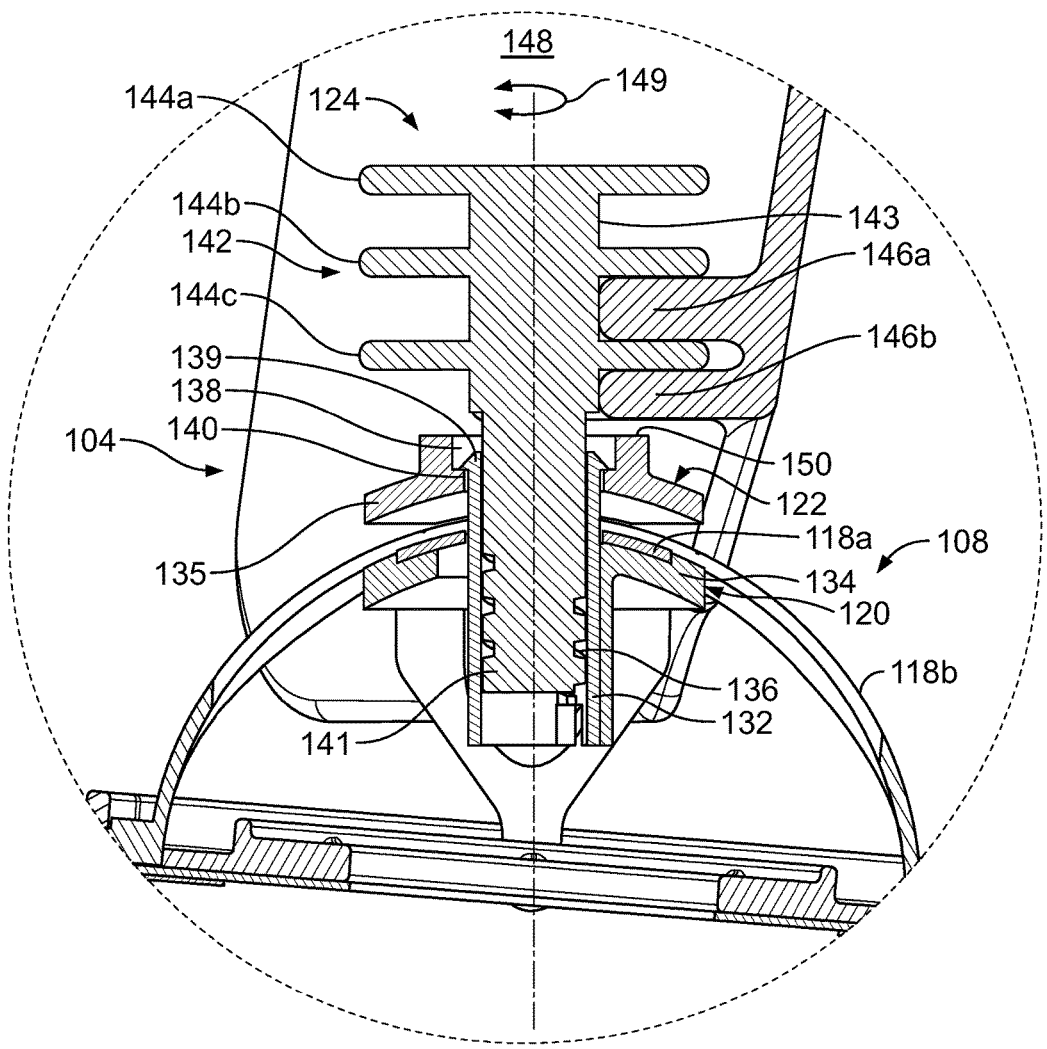
FIG. 3B is a cross-sectional view of a portion of the shielding device of FIG. 3A.

Referring to FIGS. 2, 3A and 3B, the retainer structure 108 includes a platform 116, a first yoke 118a, a second yoke 118b, a pilot member 120, a clamp member 122, and a lock knob 124. The platform 116 is a circular frame fixedly attached to the central body 110 of the substructure 106. As shown, each of the first and second yokes 118a, 118b is a semi-spherical segment having an elongated slot 126a, 126b extending along the length of the segment. The first and second yokes 118a, 118b are oriented perpendicular to one another and positioned in an overlapping manner, such that the slots 126a, 126b meet at an intersection point of the yokes 118a, 118b. The diametrically opposed ends 128a, 128b of the first and second yokes 118a, 118b are rotationally mounted to the platform 116 in a fixed position. Thus, the first yoke 118a is constrained to pivotal movement in a first direction 130a with respect to the platform 116; and the second yoke 118b is pivotally movable in a second direction 130b that is perpendicular to the first direction 130a.

Referring to FIG. 3B, the pilot member 120 includes a central shaft 132 and a convex flange 134 extending radially outward to surround the shaft 132. The shaft 132 defines a central threaded bore 136. The convex flange 134 provides a sloping upper flange surface with curvature to accommodate the semi-spherical shape of the first and second yokes 118a, 118b. The pilot member 120 is located with the convex flange 134 positioned beneath the first and second yokes 118a, 118b and an upper portion of the shaft 132 projecting through the intersection point of the slots 126a, 126b. The clamp member 122 is coupled with the pilot member 120 to retain the pilot member 120 at the intersection point of the slots 126a, 126b. The clamp member 122 includes a central opening 138 and a concave flange 135 extending radially outward to surround the opening 138. The concave flange 135 provides a sloping lower flange surface with curvature to accommodate the semi-spherical shape of the first and second yokes 118a, 118b. The clamp member 122 is located with the concave flange 135 positioned above the first and second yokes 118a, 118b. The upper portion of the shaft 132 of the pilot member 120 projects longitudinally into the opening 138 of the clamp member 122. To couple the clamp member 122 to the pilot member 120, a radial lip 139 at the upper end of the shaft 132 of the pilot member 120 provides a snap engagement with a radial shoulder 140 in the opening 138 of the clamp member 122.

Still referring to FIG. 3B, the lock knob 124 includes a shank 141 and head 142. The head 142 includes three flanges 144a, 144b, 144c, extending radially outward to surround a cylindrical body 143 coaxially aligned with the shank 141. The flanges 144a, 144b, 144c are substantially flat and spaced apart from one another longitudinally along the body 143. A lower portion of the shank 141 is threaded. The shank 141 projects longitudinally into the opening 138 of the clamp member 122 and the central bore of the shaft 132 of the pilot member 120. The threads of the central bore of the shaft 132 of the pilot member 120 mate with the threads at the lower portion of the shank 141 of the lock knob 124. Thus, the lock knob 124 is telescopically coupled with the pilot member 120 and the clamp member 122.

The lock knob 124 is movable with two degrees of freedom relative to the substructure 106 in the directions 130a, 130b permitted by the first and second yokes 118a, 118b. Movement of the lock knob 124 causes identical movement of the coupled pilot member 120. Movement of the pilot member 120 driven by the lock knob 124 causes movement by the first and second yokes 118a, 118b as the shaft 132 of the pilot member 120 interacts with the slots 126a, 126b. For example, as the pilot member 120 moves through the slot 126a of the first yoke 118b, the second yoke 118b is pulled by the shaft 132 to pivot in the second direction 130b; and vice versa. The length of the slot 126a, 126b in each respective yoke 118a, 118b bounds the movement of the pilot member 120, and therefore the lock knob 124. Freedom in the pivoting directions 130a, 130b permits the lock knob 124 to execute 360° circumduction movement resembling the conical movement of a joystick.

Figure 4A:
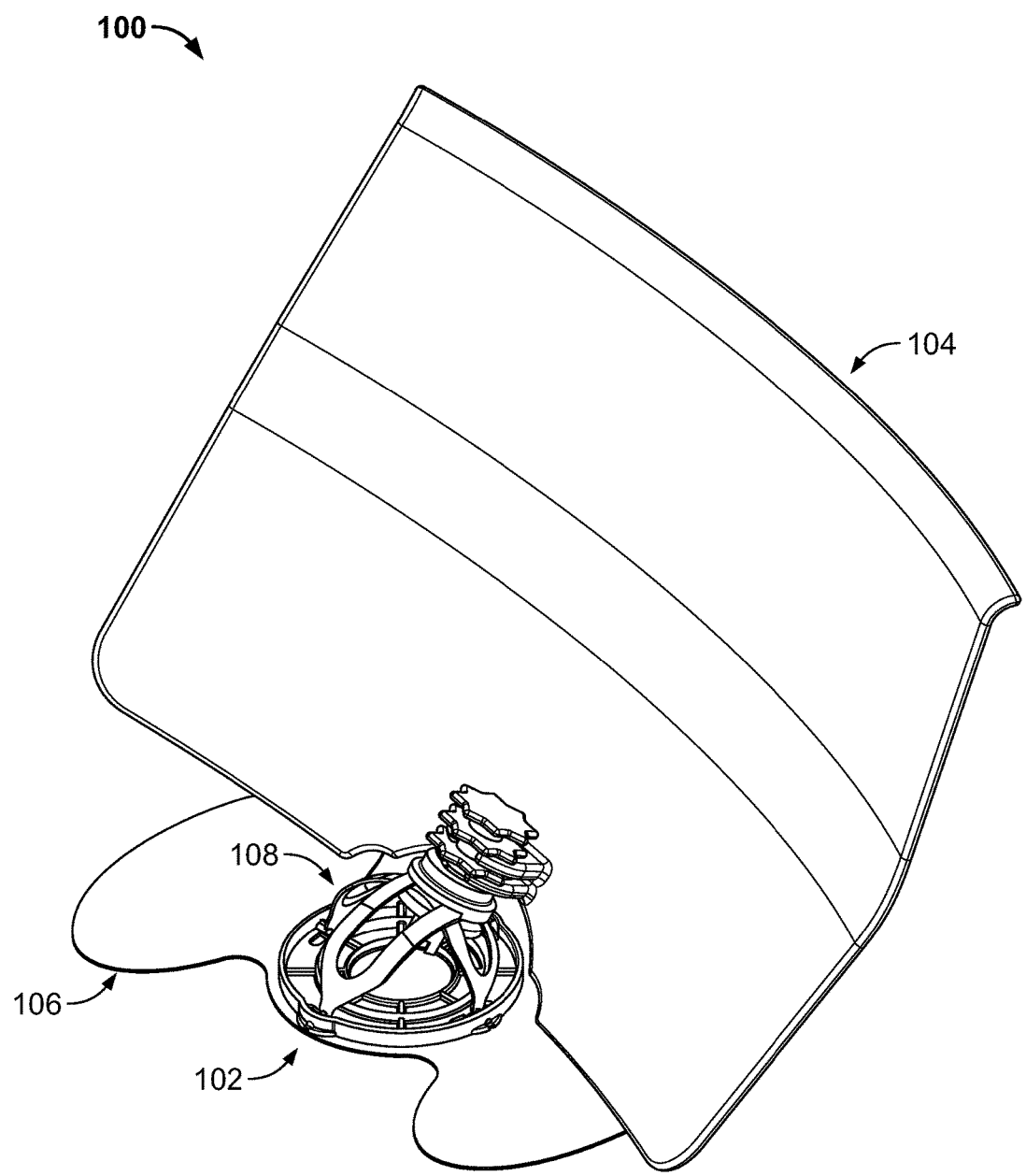
FIGS. 4A-C are perspective rear, side, and rear views of the shielding device of FIGS. 1A-C illustrated with the shield at an angled non-orthogonal position relative to the base.
Figure 4B:
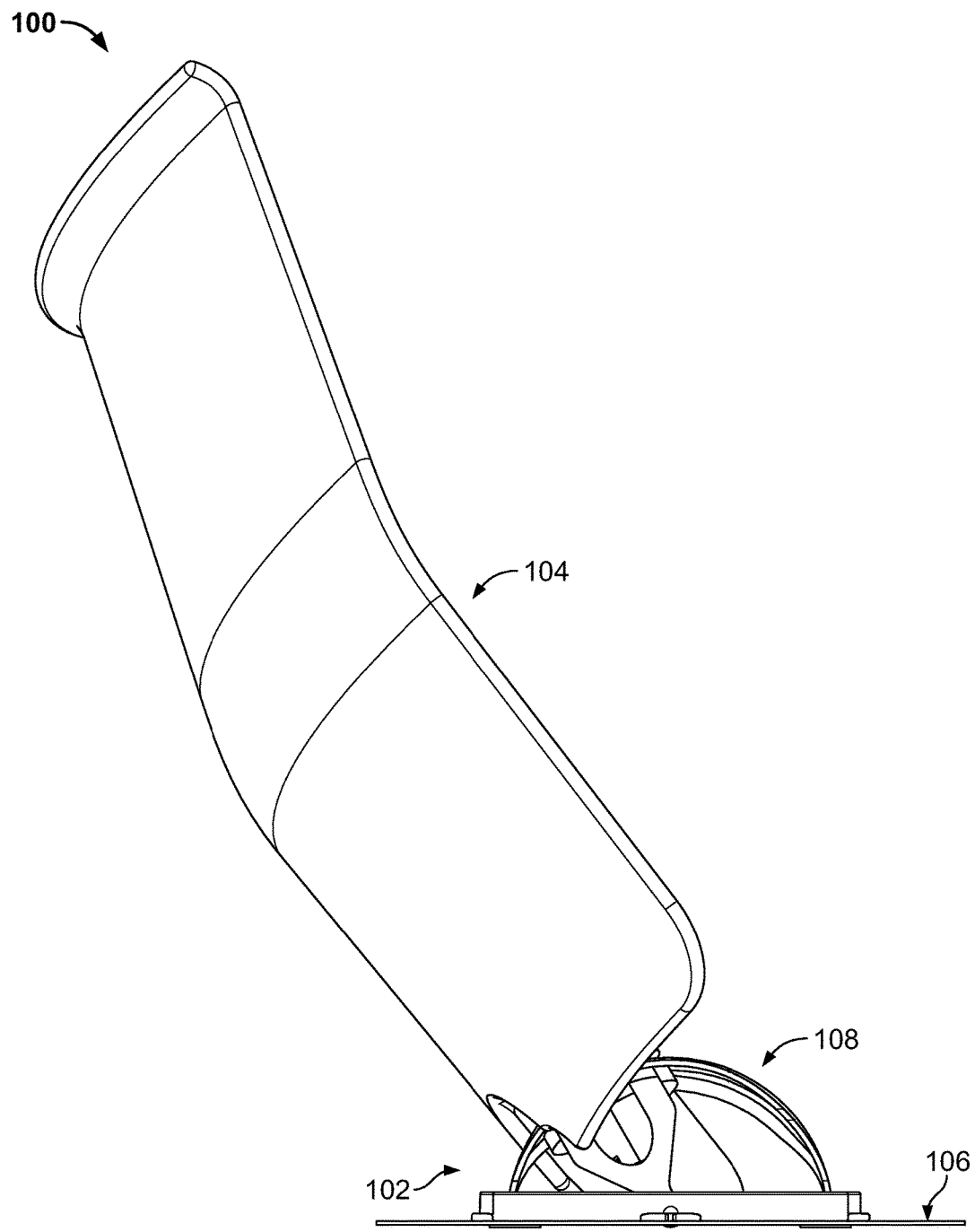
Figure 4C:
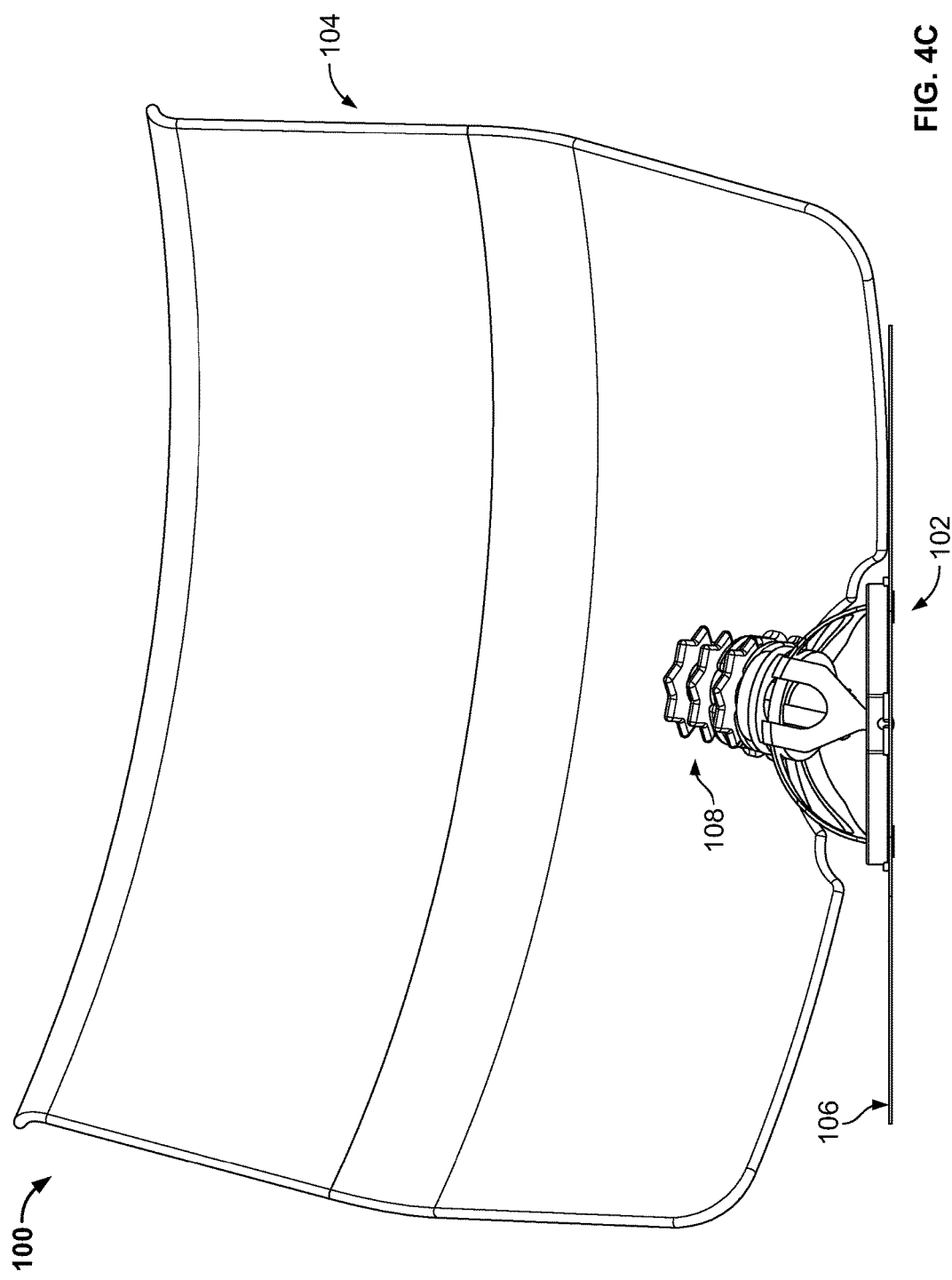

Still referring to FIG. 3B, the shield 104 is attached to the lock knob 124 by two grippers 146a, 146b that extend outward from the rear side 148 of the shield 104 to engage with the head 142 of the lock knob 124. Each of the grippers 146a, 146b includes a pair of opposing fingers formed to reach between the flanges 144b, 114c to grip the body 143 of the head 142. As shown, the first gripper 146a is positioned between the flanges 144b and 144c of the lock knob 124; and the second gripper 146b is positioned below the flange 144c. In some embodiments, the grippers 146a, 146b loosely grip the body 143 to allow 360° of rotational movement 149 in a direction about a central axis of the lock knob 124. The shield 104 can also be tilted at various angles relative to the substructure 106 by circumduction movement of the lock knob 124. FIGS. 4A-C illustrate the shield 104 tilted at an angle that is forward and sideways relative to the stationary substructure 106 of the base 102.

In some embodiments, the previously described movements of the shield 104 are permitted while the retainer structure 108 is in an unlocked condition, and prevented while the retainer structure 108 is in a locked condition. In this embodiment, the retainer structure 108 can be operated from the unlocked condition to the locked condition by adjusting the lock knob 124. For example, the lock knob 124 can be rotated (e.g., clockwise or counter clockwise) to telescopically advance the shank 141 downward through the shaft 132 of the pilot member 120 via the mating threads. Downward movement of the lock knob 124 relative to the pilot member 120 and the clamp member 122 urges the bottommost gripper 146b of the shield 104 toward the rim 150 of the opening 138 of the clamp member 122. As the lock knob 124 continues to advance downward, the clamp member 122 is pressed down against the first and second yokes 118a, 118b. The first and second yokes 118a, 118b are clamped between the concave flange 135 of the clamp member 122 and the convex flange 134 of the pilot member 120, and therefore held in a fixed position by frictional forces. With the first and second yokes 118a, 118b held stationary, circumduction movement of the lock knob 124 is prevented. Likewise, the first gripper 146a becomes clamped between the flanges 144b and 144c of the lock knob 124; and the second gripper 146b becomes clamped between the flanges 144c of the lock knob 124 and the rim 140 of the clamp member 122. Thus, frictional forces also prevent rotation of the shield 104 about the central axis of the lock knob 124. As should be understood from FIGS. 1A-4C, the shield 104 can be repeatedly operated between the locked condition and the unlocked condition (by adjusting the lock knob 124) so that the shield 104 is locked into different user-selected orientations relative to the base 102 throughout a medical procedure.

As noted above, the shield 104 can also act as a physical barrier to protect the healthcare worker. Referring to back FIGS. 1A-C, the outer edges of the shield 104 define an overall size of the shield 104—including a height "H," a width "W"—and a thickness "T" (FIG. 1A). In some embodiments, the shield 104 is provided having a contoured shape. In some embodiments, the contoured shape of the shield 104 can provide enhanced splash and spatter protection to inhibit liquids (e.g., blood and other bodily fluids) from contacting the healthcare worker during a medical procedure while simultaneously providing an ergonomic space for the healthcare worker to position his/her hands during use. In this embodiment, the shield 104 has a skewed reverse curve profile along its height, defining a short outwardly projecting lip 152 at the top of the shield 104 and an arcuate midsection 154 (FIG. 1B). During use, the shield 104 can be positioned with the front side 156 of the shield 104 facing the healthcare worker and the rear side 158 of the shield 104 facing a radiation source. In this orientation, the lip 152 and the midsection 154 are directed away from the healthcare worker to provide liquid splash and spatter protection. Further, because the midsection 154 of the shield 104 bows outward away from the healthcare worker, there is additional space for the healthcare worker to maneuver his/her hands (e.g., to perform a medical procedure and/or to adjust the lock knob 124). In this embodiment, the shield 104 is also contoured widthwise (convex from the front side 156 of the shield 104) to curve around the space where the healthcare worker is expected to position his/her hands (FIG. 1C). This configuration may provide additional protection for the healthcare worker around the space where the healthcare worker positions his/her hands. Notches 160 are provided near the bottom of the shield 104 to receive a tubular work piece (e.g., a catheter) installed on a patient (FIG. 1A).

In some embodiments, the shield 104 is capable of attenuating or deflecting the flux of electromagnetic radiation (e.g., X-Ray radiation) directed at the shield 104 by a radiation source (not shown). The effectiveness of the shield 104 directly corresponds to the radiation shielding properties of the materials used to fabricate the shield 104. The required radiation shielding effectiveness of the shield 104 may vary across different applications. For example, a less effective shield may be used applications where the healthcare worker is farther away from the radiation source, and vice versa. In some embodiments, the shield 104 can include one or more layers of radiation shielding material (e.g. a sheet of lead foil). For example, such radiation shielding layers can be sandwiched between plastic or metal reinforcement layers. In some embodiments, the shield 104 can be fabricated from a plastic material infused with suitable radiation shielding materials (e.g., materials including barium, lead, tungsten, tin, aluminum and/or any attenuating metal).

As described above, the shield 104 is carried by various components of the retainer structure 108. So, as practical matter, a tolerable weight of the shield 104 may be affected by the load bearing capacity of the retainer structure 108. Further, in applications where, for example, the shielding device 100 is supported directly on a body part of the patient, the tolerable weight of the shield 104 may be selected so as to reduce excessive strain on the patient's skin or other body part.

Factors that may be considered in designing a shield 104 of suitable weight include the volume of the shield 104 and the density of the fabricating materials. The weight of the shield 104 increases with increasing volume and/or density. The volume of the shield 104 varies according to its surface area and thickness. The volume of the shield 104 can be varied without affecting the overall size (i.e., the height "H," the width "W"), for example, by adjusting the degree of curvature of the contours (e.g., the lip 152, the midsection 154, and the widthwise contour) and/or by adjusting the thickness of the shield 104. In some applications, it may be advantageous to maintain a relative large overall size of the shield 104 to provide adequate protection to the healthcare worker. The density of the shield 104 can vary based on the specific type and amount of radiation shielding material used. For example, barium sulfate is approximately two-thirds less dense than lead, and therefore would provide a less dense, and lighter, shield if all other conditions (e.g., the volume of the shield and/or the other fabrication materials) are equal. As such, in some embodiments, the shield may comprise a material such as barium sulfate or another heavy metal material suitable for reducing or blocking radiation exposure.

In this embodiment, the volume of the shield is about 50 $cm^3$ to about 100 $cm^3$ (preferably about 71 $cm^3$ in the depicted example), and is fabricated from a plastic material infused with barium sulfate, which provides a shield density of about 1.5 $g/cm^3$ to about 2.5 $g/cm^3$ (preferably about 2.0 $g/cm^3$ in the depicted example). The height of the shield is about 5 cm to about 25 cm (preferably about 15 cm in the depicted example); the mass of the shield is about 100 g to about 200 g (preferably about 142 g in the depicted example); the thickness of the shield is about 1 mm to about 5 mm (preferably about 2.3 mm in the depicted example); the radius of curvature of the lip of the shield is about 5 mm to about 10 mm (preferably about 7.7 mm in the depicted example); the radius of curvature of the midsection of the shield is about 3 cm to about 10 cm (preferably about 5.1 cm in the depicted example); and the radius of curvature of the widthwise contour is about 10 cm to about 25 cm (preferably about 17.7 cm in the depicted example). In this embodiment, the shield weighs about 0.1 lbs to about 0.5 lbs (preferably about 0.3 lbs in the depicted example).

Figure 5A:
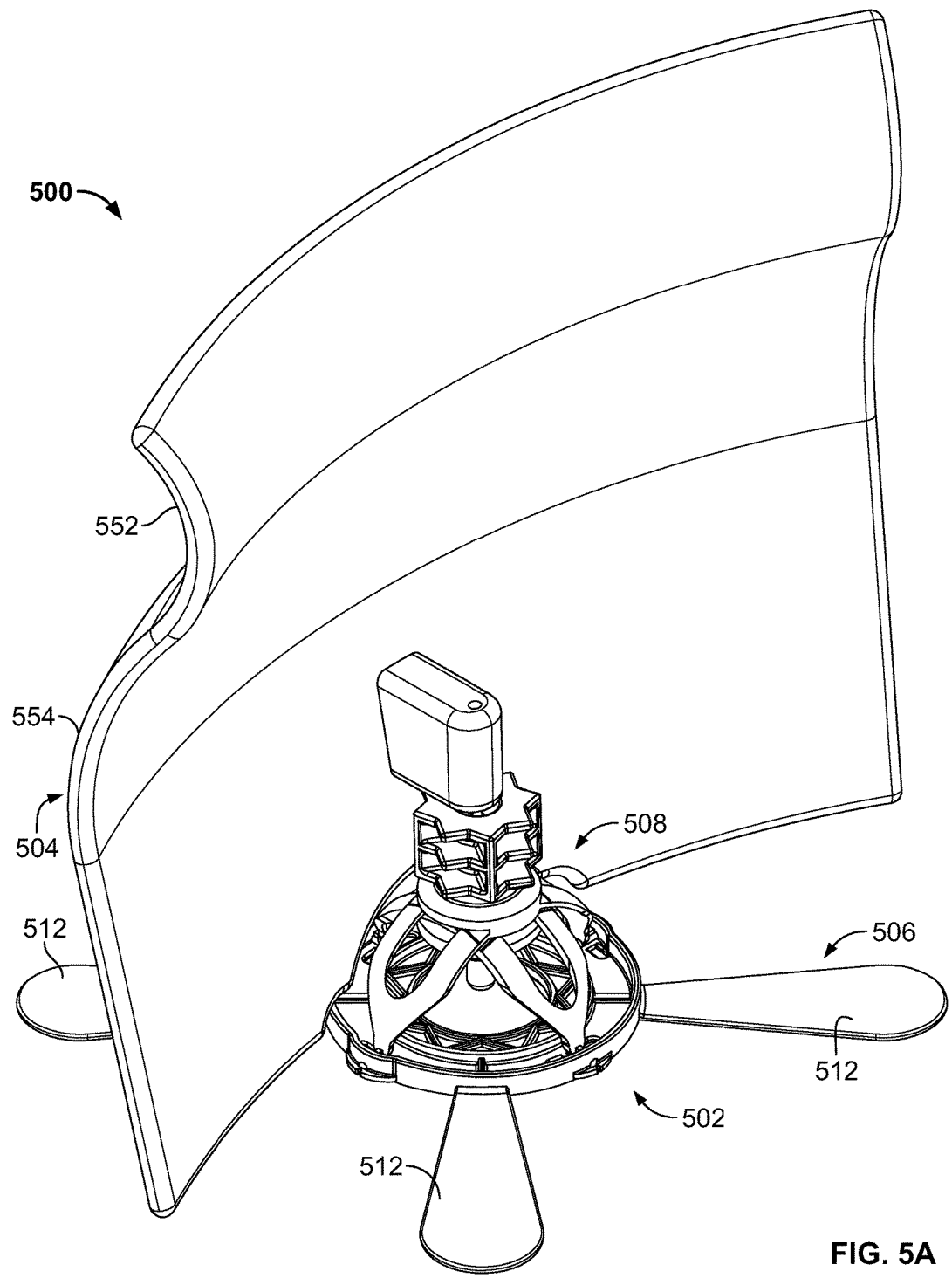
FIG. 5A is a perspective rear view of another shielding device in accordance with some alternative embodiments.
Figure 5B:
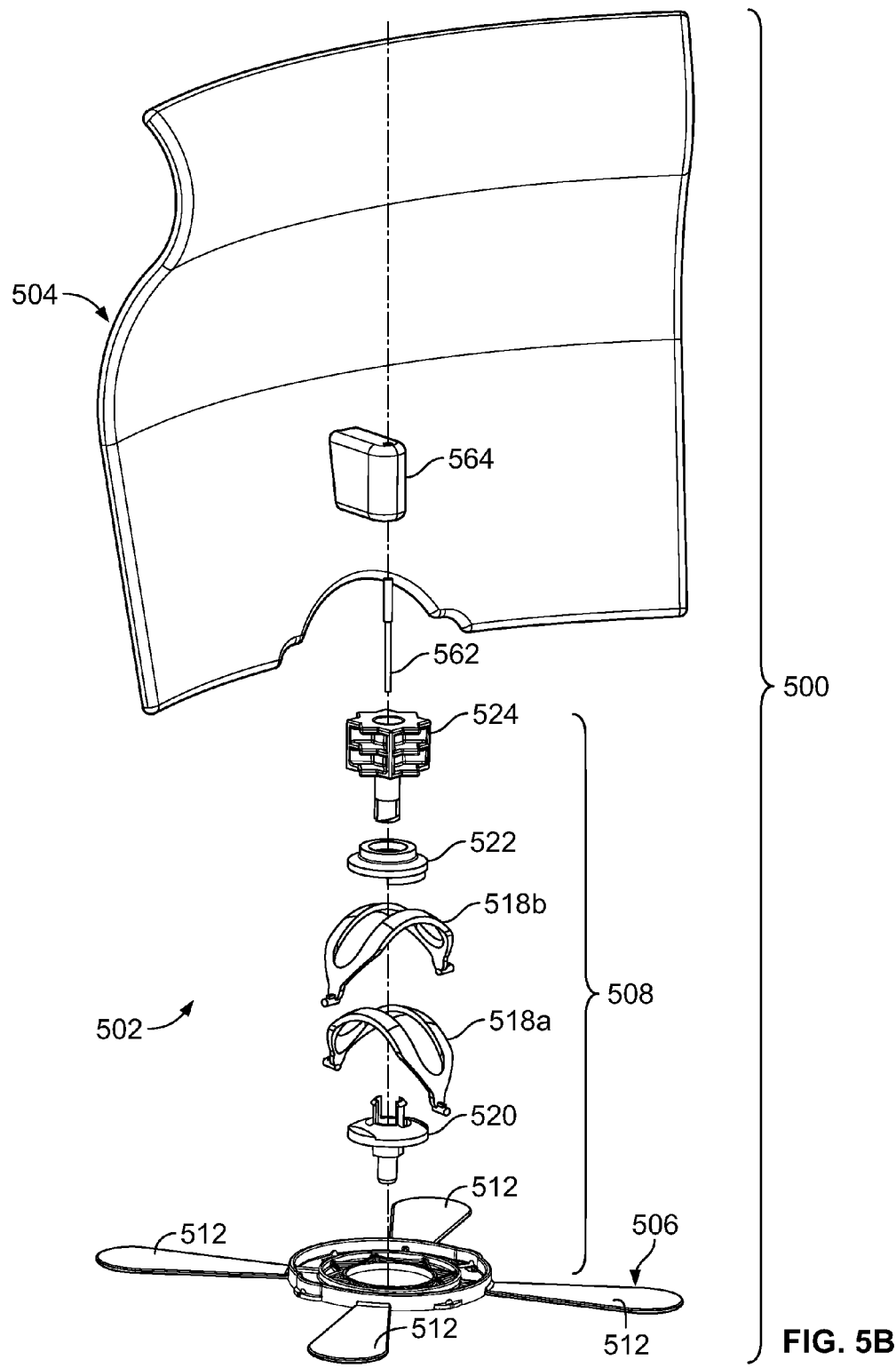
FIG. 5B is an exploded perspective rear view of the shielding device of FIG. 5A.
Figures 6E, 6F:
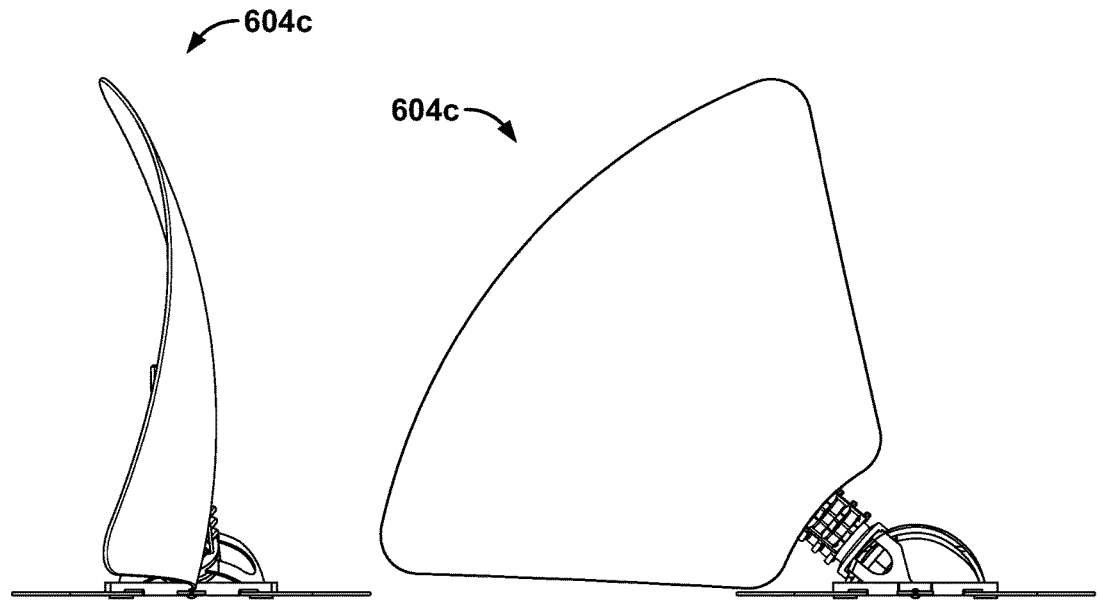
FIGS. 6E-F are side and perspective views of a shield device in accordance with additional embodiments.
Figures 6G, 6H:
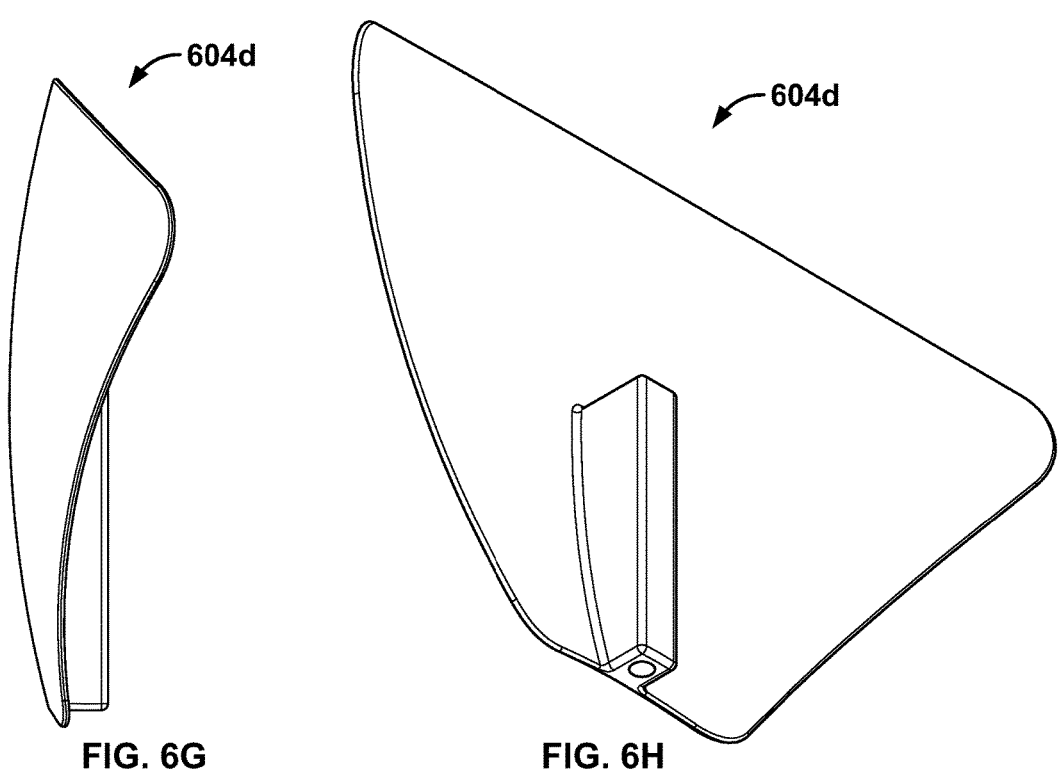
FIGS. 6G-H are side and perspective views of a shield device in accordance with further embodiments.
Figures 6I, 6J:
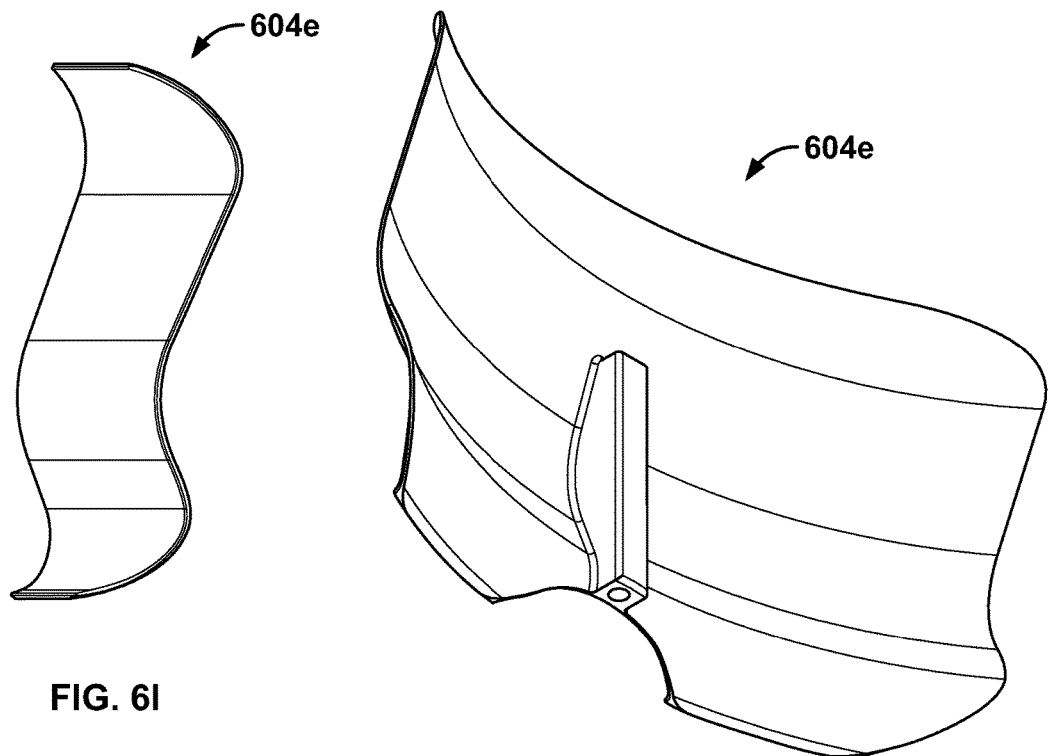
FIGS. 6I-J are side and perspective views of a shield device in accordance with additional embodiments.
Figures 6K, 6L:
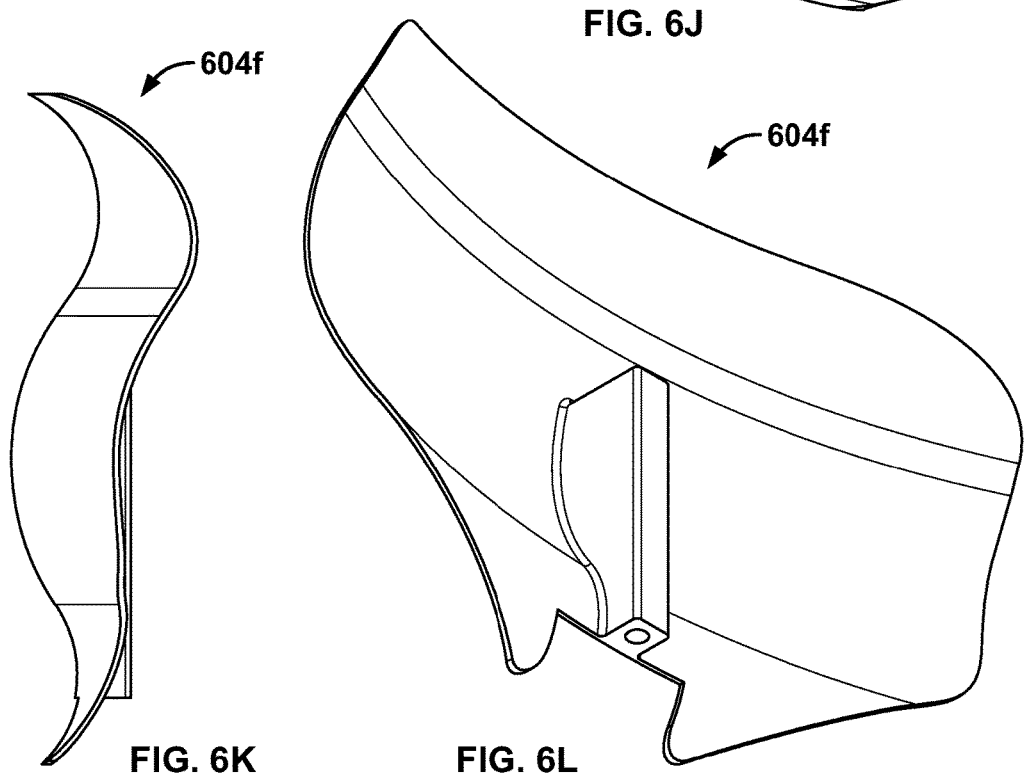
FIGS. 6K-L are side and perspective views of a shield device in accordance with further embodiments.

FIGS. 5A and 5B depict a shielding device 500 that is similar to the shielding device 100, including a base 502 and a shield 504 coupled to the base 502. In this embodiment, the contours of the shield 504 are significantly more pronounced compared to the shield 104. In particular, the lip 552 and the midsection 554 have a significantly greater degree of curvature, creating a greater surface area and therefore a greater volume (assuming constant overall size and thickness). Thus, if all other conditions are equal, the shield 504 would have a greater weight than the shield 104.

The base 502 includes a substructure 506 and a retainer structure 508. In this embodiment, the substructure 506 includes four radial legs 512. In some embodiments, the legs 512 are flexible and can be bent out of plane to follow the shape of a supporting object. The retainer structure 508 includes a platform 516, a first yoke 518a, a second yoke 518b, a pilot member 520, a clamp member 522, and a lock knob 524. Generally, these components may be assembled to function generally as described above. However, in this embodiment, the shield 504 is coupled to the lock knob 524 by a coupling pin 562. In particular, the lock knob 524 includes a central bore for receiving the lower end of the coupling pin 562; and the upper end of the coupling pin 562 is received by a collar housing 564 on the rear side 548 of the shield 504.

FIGS. 6A-6L depict various example shields 604a-604f that may be suitable for use in various embodiments of a suitable shielding device. As described above, the overall shape and size, as well as the contours of the various shields 604a-604f may affect the volume, and therefore the weight, of the respective shield for a given density of the fabricating materials. The configuration of the shield (e.g., the size, shape, contour, thickness, density) may vary across different implementations based on the desired application. For example, applications requiring protection from a relative high degree of scatter radiation may involve a shield that is relatively large in overall size to provide broad coverage. In this case, the weight of the shield can be maintained within tolerable limits, for example, by fabricating the shield with a less dense material and/or by fabricating the shield with less severe counters and/or relatively low thickness.

Figure 7:
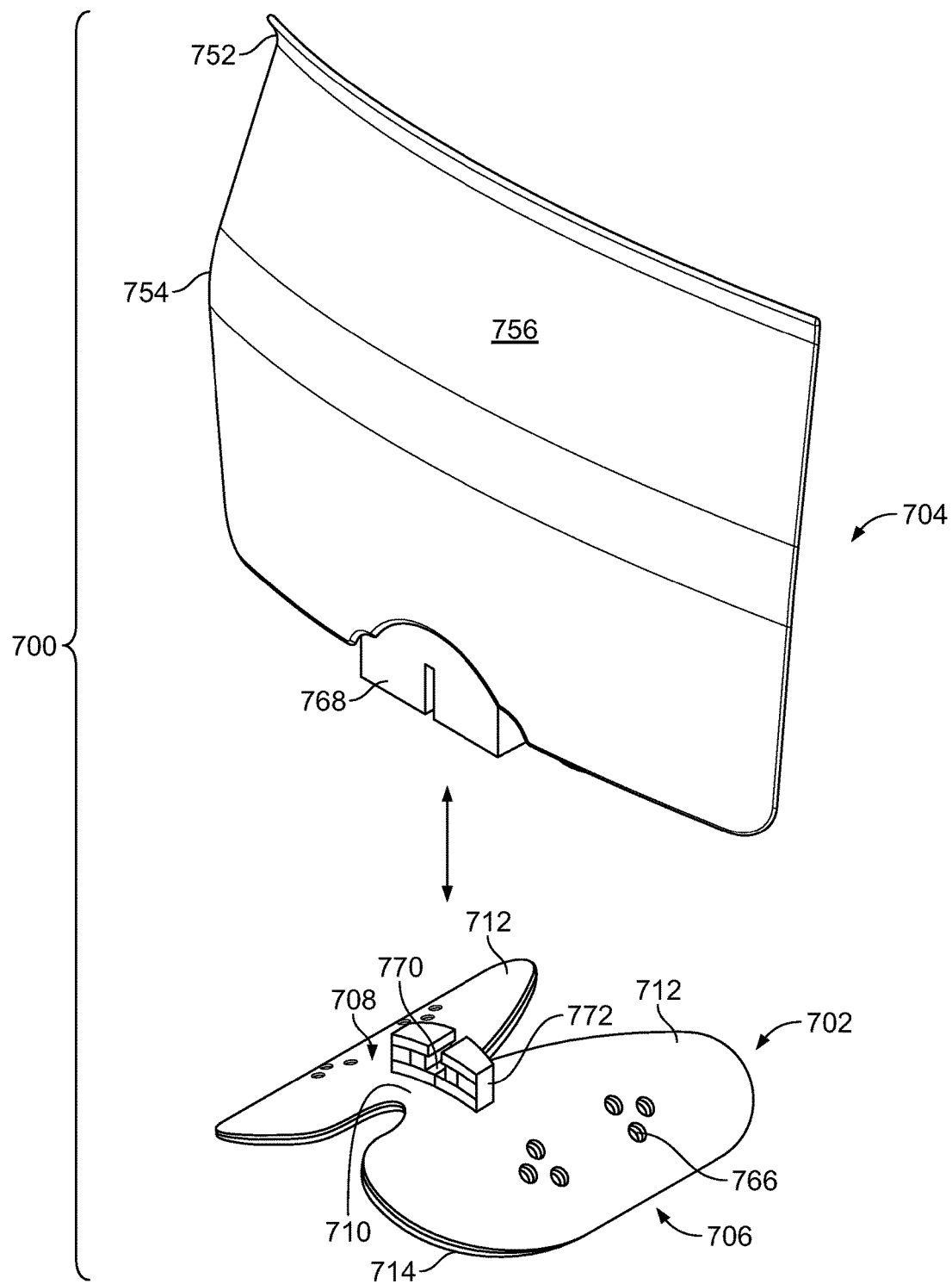
FIG. 7 is an exploded perspective front view of a second alternative shielding device in accordance with some embodiments.

FIG. 7 depicts yet another shielding device 700 including a base 702 and a shield 704 coupled to the base 702. The shield 704 is similar to the shield 104, having a contoured shape defining a reverse curve profile including an outwardly projecting lip 752 and an arcuate midsection 754. The shield 704 is also contoured widthwise, appearing convex from the front side 756 of the shield 704. As noted above, in some embodiments, the contoured shape of the shield 704 can provide splash and spatter protection to inhibit liquids from contacting the healthcare worker. Further, in some embodiments, the contoured shape of the shield 704 can provide an ergonomic space for the healthcare worker to position his/her hands during use.

The base 702 includes a substructure 706 and a retainer structure 708. As in previous embodiments, during use of the shielding device 700, the substructure 706 supports the base 702 on the surface of an object (not shown) and the retainer structure 708 couples the base 702 to the shield 704. In this embodiment, the substructure 706 includes a butterfly-shaped member having opposing tapered oblong wings 712 connected by a narrow body 710. In some embodiments, the substructure 706 can include a compliant member capable of conforming to various contours and corners of the supporting object. For example, in this embodiment, the wings 712 can be bent out of plane to follow the shape of the object. In some embodiments, the substructure 706 can include a malleable wire frame to reinforce the compliant member. In some embodiments, the substructure 706 is fabricated from one or more materials that are suitable for medical applications (e.g., biocompatible metallic and/or polymeric materials). In some embodiments, a bottom surface 714 of the substructure 706 can include an adhesive material suitable for temporarily adhering the base 702 to the supporting object. The adhesive can be a medical grade adhesive resistant to water, blood, and other bodily fluids, and releasable by alcohol (e.g., ethyl alcohol). In some embodiments, the substructure 706 is fabricated from one or more materials capable of accepting an infusion of radiation shielding material (e.g., material including barium, lead, tungsten, tin, aluminum and/or any attenuating metal). In some embodiments, the substructure 706 can include a laminated multi-layer construction. For example, the substructure 706 can include a skin-friendly underlayer (e.g., a foam layer) bonded to a reinforcing overlayer (e.g., a flexible metal or plastic layer).

As shown, the substructure 706 further includes a plurality of apertures 766 that extend through the material to expose the supporting object. During use, a healthcare worker can suture the substructure 706 to the object through one or more of the apertures 766, for example, if the adhesive on the bottom surface 714 is unsuitable of ineffective for the particular applications. As one example, the healthcare worker can suture the substructure to a patient's skin through the apertures 766 if the patient is allergic to the adhesive.

The retainer structure 708 is attached to the substructure 706 across the narrow body 710 between the wings 712. The retainer structure 708 can be attached to a coupling member 768 provided at the bottom end of the shield 704 to couple the shield 704 to the base 702. In some embodiments, the coupling member 768 can be snap-fit or press-fit to the retainer structure 708 to secure the shield 704 to the base 702. In this embodiment, the retainer structure 708 includes a slot 770 appropriately shaped and sized for receiving a tubular work piece (e.g., a catheter, a drain, an intravenous line) and a lock mechanism 772 for securing the work piece in the slot 770. For example, if shielding device 700 is supported on an object proximate a catheter exit site, the catheter can be positioned lengthwise in the slot 770 and held in place by the lock mechanism 772 to inhibit the unintentional release of the catheter from the patient. The slot 770 and the lock mechanism 772 can be designed to accommodate a particular size or a range of sizes. In some embodiments, the slot 770 and the lock mechanism 772 are designed to accommodate tubular work pieces in the range of about 4 French (1.33 mm) to about 12 French (4 mm). In some embodiments, the lock mechanism 772 includes a spring-loaded clamp (not shown) that grips the work piece with sufficient force to inhibit unintentional release of the work piece. In some embodiments, the work piece can be secured and/or released from the lock mechanism 772 without removing the shield 704 from the base 702, which may allow the healthcare worker to adjust the work piece during a medical procedure without being exposed to radiation. In some embodiments, a shielding plug (not shown) can be installed on the retainer structure 708 to block fluid and/or radiation from penetrating through the slot 770 and the lock mechanism 772 when no work piece is present.

Figure 8:
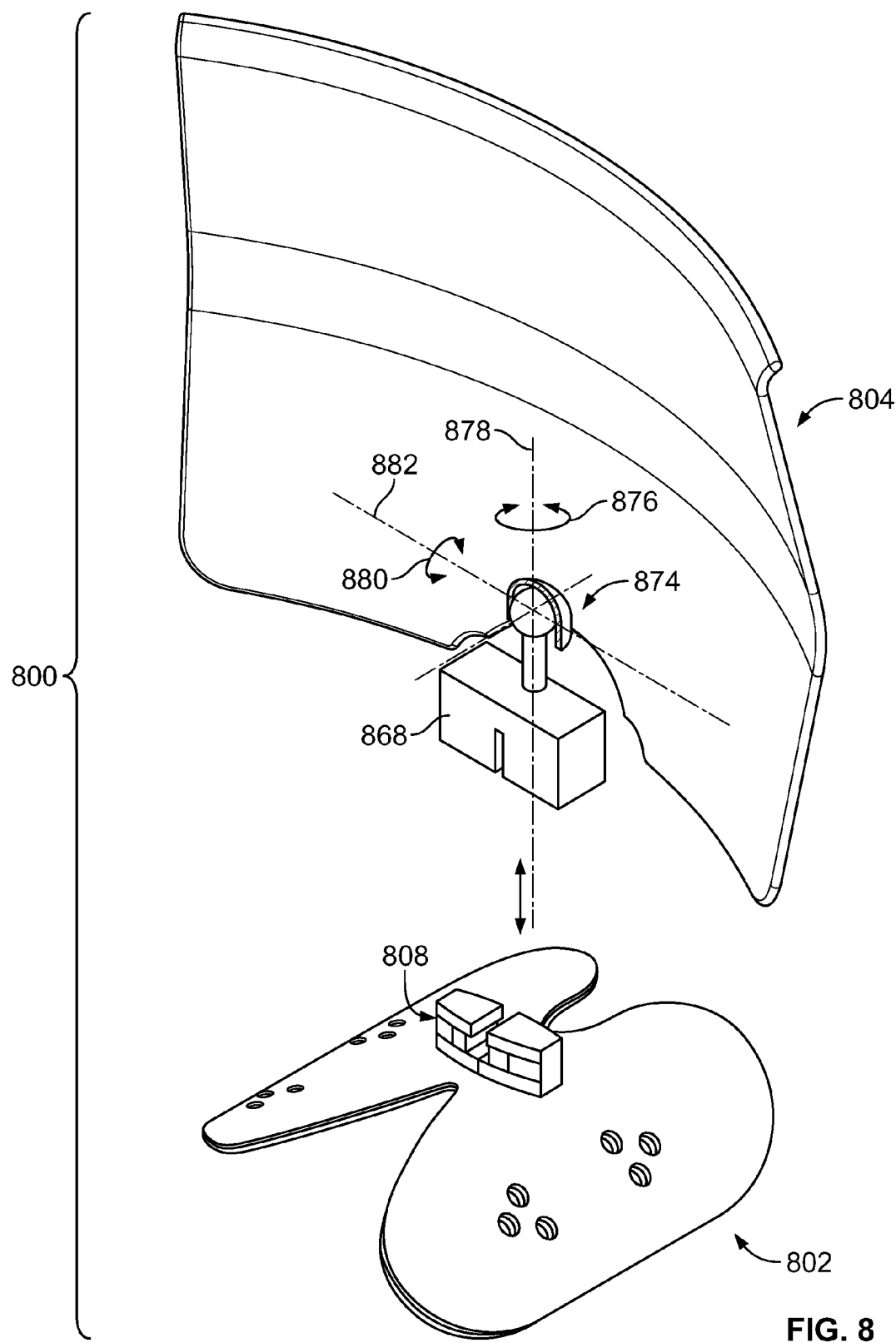
FIG. 8 is an exploded perspective front view of a third alternative shielding device in accordance with some embodiments.

FIG. 8 depicts a shielding device 800 that is similar to the shielding device 700, including a base 802 and a shield 804 coupled to the base 802 In this embodiment, the shield 804 is mounted to a coupling member 868 by a ball and socket joint 874. The coupling member 868 attaches the shield 804 to the retainer structure 808 of the base 802. The ball and socket joint 874 permits movement of the shield 804 relative to the base 802 within at least two degrees of freedom. In this embodiment, the ball and socket joint 874 permits rotational movement 876 of the shield 804 about an axis 878 substantially perpendicular to the base 802, and articulating movement 880 about an axis 882 substantially perpendicular to the axis of rotation. As shown, the articulating movement 880 tilts the shield 804 forward and backward relative to the base 802. In some embodiments, the ball and socket joint 874 permits 360° of rotation of the shield 804. In some embodiments, the ball and socket joint 874 limits articulation of the shield 804 to plus or minus 30°.

Figure 9:
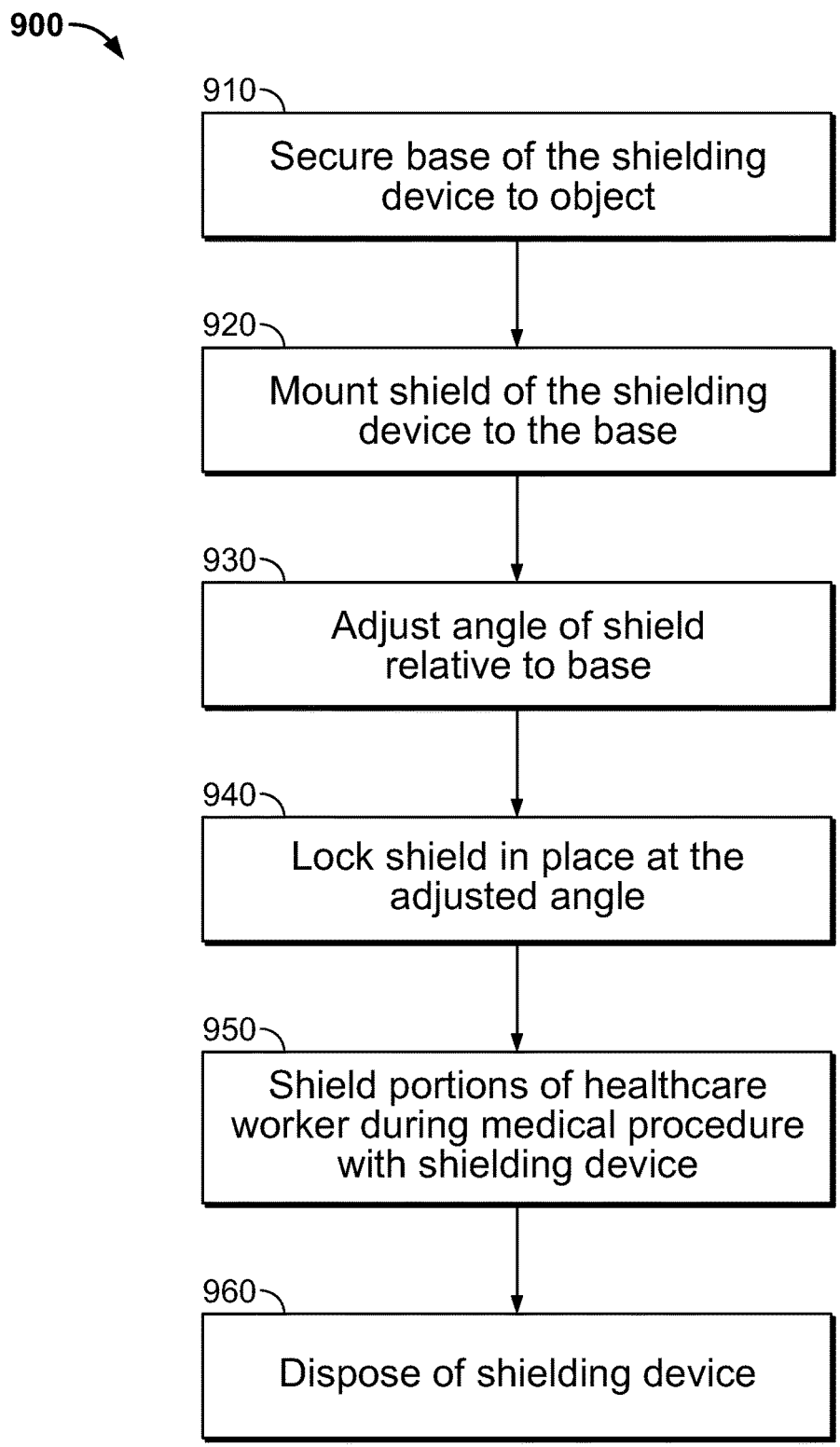
FIG. 9 is a flow chart describing a process of using a shielding device in accordance with some embodiments.

Referring now to FIG. 9, a suitable shielding device (e.g., shielding device 100, 500, 700 and 800) can be operated (e.g., by a healthcare worker) to implement a process 900 of shielding radiation and/or liquid from a healthcare worker during a medical procedure. Note that the process 900 does not require the particular order of operations shown in FIG. 9 and described below to achieve desirable results. In addition, other operations may be provided, or eliminated, to the process 900 without departing from the scope of the present disclosure.

In operation 910, a base of the shielding device can be coupled to an object. The object may include an exposed body part of a patient or any other structure that is capable of carrying the base and an attached shield. In some embodiments, the base can be coupled to the object by an adhesive layer on a bottom surface of the base. In some embodiments, the base can be sutured to the object.

In operation 920, a shield of the shielding device can be coupled to the base. For example, the shield can be attached to a retainer structure of the base. In some embodiments, the retainer structure may include a lock knob and the rear side of the shield can include grippers that engage the head of the lock knob (e.g., shielding device 100). In some embodiments, the shield can be coupled to the lock knob by a coupling pin (e.g., shielding device 500). The lower end of the coupling pin is received in a central bore of the lock knob, and the upper end of the coupling pin is received by a collar housing on the rear side of the shield. In some embodiments, a coupling member at the bottom end of the shield can be press-fit or snap-fit to the retainer structure (e.g., shielding device 700). In some embodiments, a malleable stem or a clasp can be used to couple the shield to the base.

Optionally, in operation 930, the angle of the shield relative to the base of the shielding device and the object can be adjusted. In some embodiments, the coupling between the shield and the base permits movement of the shield within three degrees of freedom relative to the base (e.g., shielding device 100). In this case, the angle of the shield relative to the base can be adjusted by rotation and circumduction movement of the shield relative to the base. In some embodiments, the coupling permits movement of the shield within at least two degrees of freedom (e.g., shielding device 800). In this case, the angle of the shield relative to the base can be adjusted by rotation and articulation movement of the shield relative to the base. Optionally, in operation 940, the shield can be locked in place at the angle. For example, in embodiments where the shield includes a lock knob threaded to a pilot member (e.g., shielding device 100 and 500), the lock knob can be rotated to clamp the shield in place.

In operation 950, the medical procedure can be conducted while the shield inhibits radiation and/or liquid from contacting the healthcare worker. In some embodiments, the shield can be fabricated from one or more suitable radiation shielding materials. In some embodiments, the shield can be appropriately contoured to block liquid splash and splatter that may occur during the medical procedure. Optionally, in operation 960, the shielding device is removed from the supporting object and disposed of, for example, to prevent the spreading of pathogens between patients and/or healthcare workers.

The use of terminology such as "front," "rear," "top," "bottom," "over," "above," and "below" throughout the specification and claims is for describing the relative positions of various components of the system and other elements described herein. Similarly, the use of any horizontal or vertical terms to describe elements is for describing relative orientations of the various components of the system and other elements described herein. Unless otherwise stated explicitly, the use of such terminology does not imply a particular position or orientation of the system or any other components relative to the direction of the Earth gravitational force, or the Earth ground surface, or other particular position or orientation that the system other elements may be placed in during operation, manufacturing, and transportation.

A number of embodiments of the invention have been described. Nevertheless, it will be understood that various modifications may be made without departing from the scope of the invention.

The invention claimed is:

1. A radiation shielding device, comprising:
   a radiation shield; and
   a base comprising:
      a substructure attachable to an object; and
      a retainer structure attachable to the radiation shield, wherein the retainer structure comprises an adjustable coupling operable between an unlocked condition in which an angular position of the shield is adjustable to a user-selected position, and a locked condition in which the angular position of the shield is substantially fixed;
      wherein the retainer structure comprises a lock knob threadingly engaged with the adjustable coupling to operate the coupling between the locked and unlocked conditions;
      wherein the lock knob is engageable with the shield; and
      wherein the lock knob comprises a head including a plurality of flanges extending radially outward from a cylindrical body, and wherein the shield comprises one or more grippers to reach between the flanges and grip the cylindrical body.

2. The shielding device of claim 1, wherein the retainer structure comprises a clamp member bearing against the lock knob when the coupling is in the locked condition to fix the angular position of the shield by frictional forces.

3. The shielding device of claim 2, wherein the adjustable coupling permits movement of the shield with at least two degrees of freedom.

4. The shielding device of claim 3, wherein the permitted movement of the shield includes circumduction movement.

5. The shielding device of claim 4, wherein the shield is contoured widthwise in a convex orientation relative to a front side of the shield.

6. The shielding device of claim 5, wherein the shield defines an outwardly projecting lip at the top of the shield and a broad arcuate midsection.

7. The shielding device of claim 6, wherein a bottom portion of the shield comprises at least one notch to receive a tubular work piece installed on a patient.

8. The shielding device of claim 7, wherein a radius of curvature of the lip of the shield is about 5 mm to about 10 mm, and the radius of curvature of the midsection is 3 cm to 10 cm.

9. The shielding device of claim 8, wherein an overall size of the shield is sufficient to cover an area where a healthcare worker would position his/her hands during a medical procedure.

10. The shielding device of claim 9, wherein the radiation shield comprises a barium sulfate, and the radiation shield has a nominal density of 1.5 g/cm3 to 2.5 g/cm3.

* * * * *